(12) United States Patent
Laufer

(10) Patent No.: US 10,751,131 B2
(45) Date of Patent: Aug. 25, 2020

(54) SYSTEMS, DEVICES AND METHODS FOR RESUSCITATION

(71) Applicant: Michael D. Laufer, Menlo Park, CA (US)

(72) Inventor: Michael D. Laufer, Menlo Park, CA (US)

(73) Assignee: Michael D. Laufer, Menlo Park, CA (US)

( * ) Notice: Subject to any disclaimer, the term of this patent is extended or adjusted under 35 U.S.C. 154(b) by 637 days.

(21) Appl. No.: 15/373,034

(22) Filed: Dec. 8, 2016

(65) Prior Publication Data

US 2017/0165007 A1 Jun. 15, 2017

Related U.S. Application Data

(60) Provisional application No. 62/265,336, filed on Dec. 9, 2015.

(51) Int. Cl.
| | | |
|---|---|---|
| *A61B 34/20* | (2016.01) | |
| *A61M 25/10* | (2013.01) | |
| *A61M 25/06* | (2006.01) | |
| *A61M 5/142* | (2006.01) | |
| *A61M 25/00* | (2006.01) | |
| *A61M 5/14* | (2006.01) | |

(52) U.S. Cl.
CPC ............ *A61B 34/20* (2016.02); *A61M 5/142* (2013.01); *A61M 25/0029* (2013.01); *A61M 25/0606* (2013.01); *A61M 25/10* (2013.01); *A61M 25/104* (2013.01); *A61M 5/14* (2013.01); *A61M 2025/0031* (2013.01); *A61M 2025/1052* (2013.01); *A61M 2025/1063* (2013.01); *A61M 2205/58* (2013.01); *A61M 2205/581* (2013.01); *A61M 2205/582* (2013.01); *A61M 2205/583* (2013.01)

(58) Field of Classification Search
CPC ....... A61B 34/20; A61M 5/142; A61M 25/10; A61M 25/0029; A61M 2025/1063; A61M 2025/1052; A61M 2025/0031
See application file for complete search history.

(56) References Cited

U.S. PATENT DOCUMENTS

| | | |
|---|---|---|
| 5,041,125 A | 8/1991 | Montano, Jr. |
| 5,042,976 A | 8/1991 | Ishitsu et al. |
| 5,045,061 A | 9/1991 | Seifert et al. |
| 5,049,131 A | 9/1991 | Deuss |

(Continued)

OTHER PUBLICATIONS

Safer. P, et al., "Emergency cardiopulmonary bypass for resuscitation from prolonged cardiac arrest," Am. J. Emerg. Med. vol. 8, Issue 1, 55-67 (Jan. 1990).

(Continued)

*Primary Examiner* — Bradley J Osinski
(74) *Attorney, Agent, or Firm* — Levine Bagade Han LLP

(57) ABSTRACT

Methods, devices, systems of resuscitating a patient including accessing an arterial vessel positioning a catheter into the arterial vessel advancing the catheter through the arterial vessel to position it below a vessel supplying blood to a heart and a brain expanding an expandable portion of the catheter to prevent blood from flowing past the expanded portion and infusing a substance retrograde into the artery within the arterial section between the bean and the expanded portion of the catheter.

9 Claims, 8 Drawing Sheets

(56) References Cited

U.S. PATENT DOCUMENTS

| | | |
|---|---|---|
| 5,049,132 A | 9/1991 | Shaffer et al. |
| 5,216,032 A | 6/1993 | Manning |
| 5,334,142 A | 8/1994 | Paradis |
| 5,678,570 A | 10/1997 | Manning |
| 2007/0129752 A1* | 6/2007 | Webler .................. A61F 2/013 606/200 |
| 2014/0142548 A1 | 5/2014 | Manning et al. |

OTHER PUBLICATIONS

Anstadt, M. et al., "Direct mechanical ventricular actuation: A review," Resuscitation 21, 7-23 (1991).

Bartlett, R. et al., "Comparative study of three methods of resuscitation: Closed-chest, open-chest manual, and direct mechanical ventricular assistance," Ann. Emerg. Med. 13:9 (Part 2), 773-777 (Sep. 1984).

\* cited by examiner

SYSTEMS, DEVICES AND METHODS FOR RESUSCITATION

RELATED APPLICATION DATA

This application is a non-provisional of U.S. Provisional Application No. 62/265,336 filed Dec. 9, 2015, the entirety of which is incorporated by reference. This application also incorporates by reference U.S. Provisional No. 61/727,302 filed on Nov. 16, 2012, entitled RESUSCITATION SYSTEM AND METHOD OF USE; and U.S. patent application Ser. No. 14/083,192 filed on Nov. 18, 2013, entitled SYSTEMS, DEVICES AND METHODS FOR RESUSCITATION.

FIELD OF THE INVENTION

The present invention relates to an injection system for administering medical substances into tissue. Variations of the device and method described herein allow for an automated injector for administration of medications under the skin or into the muscle of patients. Further variations include injection systems designed to reside on an individual where injection of the substance can occur when needed and on-demand.

BACKGROUND

The survival rate is relatively low for a person, whether in a medical setting or elsewhere, is relatively low. One of the reasons for the high mortality rate is that cardiopulmonary resuscitation (CPR), one of the primary resuscitation methods, induces little forward blood flow. Although certain drugs, such as epinephrine, can improve vital organ blood flow during CPR, these drugs are administered almost exclusively into a vein; as such, the drug must circulate to and through the heart and lungs before arriving at the peripheral arteries where their primary beneficial pharmacological effects occur. During this low blood state of CPR, the heart and brain receive very limited blood flow blood that may fail to sustain cellular survival.

Invasive techniques such as open-chest cardiac massage (OCCM), direct mechanical ventricular assistance (DMVA), and cardiopulmonary bypass (CPB) can provide better vital organ blood flow. See generally R. Bartlett et al., Ann. Emerg. Med. 13(Part 2), 773-777 (1984); M. Anstadt et al., Resuscitation 21,7-23 (1991); P. Safar et al., Am. J. Emerg. Med. 8, 55-67 (1990). However, adaptation of these techniques for widespread use, particularly in a setting outside a hospital, is unrealistic. In most cases, the response time that would enable significant neurologic recovery would likely expire before these techniques could be employed in a typical emergency.

Selective aortic arch perfusion (SAAP) is a technique designed to provide relatively isolated perfusion of the heart and brain in patients suffering cardiac arrest. SAAP is typically performed by inserting a large lumen balloon occlusion catheter, percutaneously or by surgical cutdown, into a femoral artery and then advancing the catheter tip to the descending aortic arch, preferably just distal to the left subclavian artery. With the SAAP catheter balloon inflated to prevent or restrict distal aortic flow, the coronary and cerebral circulations can be relatively selectively perfused with a solution infused via the lumen of the SAAP catheter. The infused solution is typically an oxygenated blood substitute, such as a perfluoro carbon emulsion or polymerized hemoglobin solution that contains various agents capable of reversing ischemic metabolic processes, restoring peripheral vascular resistance, correcting hemostatic derangements, and limiting reperfusion-induced cellular damage. For example, vasoconstrictors such as epinephrine are beneficial. Perfusion with such a solution can enhance return of spontaneous cardiac function and facilitate neuronal functional recovery. Catheters intended to occlude the descending aorta are disclosed by Manning, U.S. Pat. Nos. 5,678,570, 5,216,032, and Paradis, U.S. Pat. No. 5,334,142 each of which is incorporated by reference herein.

Although research indicates that SAAP shows promise, the technique has certain shortcomings. SAAP is a volume loading procedure and, as such, is volume limiting. When excess volumes of protective solution are infused, as may happen if an initial SAAP infusion is insufficient to resuscitate the patient and is followed by subsequent infusions, pulmonary congestion and edema can result, each of which can have a significant adverse effect on pulmonary oxygenation. The conventional devices do not optimally address avoidance of volume overload during SAAP.

SUMMARY OF THE INVENTION

The devices and methods described herein improve shortcomings in SAAP treatment. The disclosure includes methods and devices for resuscitating a patient. For example, the method can include accessing an arterial vessel; positioning a catheter into the arterial vessel; advancing the catheter through the arterial vessel to position it below a vessel supplying blood to a heart and a brain; expanding an expandable portion of the catheter to prevent blood from flowing past the expanded portion; infusing a substance retrograde into the artery within the arterial section between the heart and the expanded portion of the catheter.

In a variation of the method, accessing the arterial vessel involves identifying the location of the arterial vessel by a technique selected from the group consisting of a) feeling for a pulse and inserting the access device at the pulse; b) using ultrasound; c) using an electric field; d) using a magnetic field disturbance; and e) using tissue density differences.

In another variation, where positioning the catheter further comprises placing a needle through the skin and overlying tissue into the artery; placing a wire through the needle; and placing the catheter over the needle or over the wire after removing the needle.

The method can also further comprise determining the position below the vessel supplying blood to the heart and the brain is determined by a technique selected from the group consisting of: a) determining the distance from the access site to a desired position external to the patient and advancing the catheter to said predetermined distance; b) using xray to place the catheter into appropriate position and to verify that the catheter is in appropriate position; c) detecting a signal from the catheter (light, sound, ultrasonic, heat, cold, electromagnetic to determine placement position.

In another variation, expanding the expanded portion comprises a device selected from the group consisting of a) a balloon catheter; b) a catheter with an umbrella structure; c) a catheter having a mechanically expanding spheroid.

The substances used in the methods and device can include a) blood; b) oxygen carrier such as a perflourocarbon; c) calcium; d) EDTA; e) saline; f) cooling or warming fluid.

The retrograde infusion can be continuous or pulsatile.

A variation of the method includes the retrograde infusion supplied at a rate and or pressure sufficient to close the aortic valve.

The devices described herein also include a catheter capable of performing the methods described here. Such a catheter can have the following characteristics: a) a proximal end; a distal end; a lumen connecting the proximal end to the distal end; an occluding part at the distal end that can be activated from outside the patient to occlude the flow of fluid on the outside of the lumen past itself.

The occluding part of claim can be one of the following: a balloon; an expandable covered cage; side port suction that draws vessel around the part.

In a variation, the device can include a pump to inject fluid from the proximal end of the device described herein such that it flows to the distal end of the catheter and into the blood vessel in a retrograde direction so as to increase the pressure in the vessel and close a valve such as the aortic valve when the vessel is the aorta, thereby directing flow of the injected fluid into side branches of the vessel such is into the coronary arteries and carotid arteries.

The disclosure also includes an infusion substance that consists of at least one of the following: saline; oxygen carrier such as blood or a fluorocarbon based oxygen carrier; epinephrine; atropine; calcium chelator such as EDTA, calcium salts such as calcium gluconate and calcium carbonate.

Another device includes a device for locating and cannulating a blood vessel consisting of a channel through which a needle or catheter can be placed from the outside of a patient to the inside of a blood vessel, a feedback system that provides information to the user that further makes it possible for the vessel to be located and for the catheter to be placed therein. Such a feedback method can include a least one of the following: a light pattern; a color change; a screen showing an image; a sound; a vibration; a temperature change;

The light pattern described herein can include light changing from red to green when the device of claim 5 is correctly placed over a blood vessel to allow cannulation.

BRIEF DESCRIPTION OF THE DRAWINGS

FIG. 7B illustrates the valve in a closed position.

DETAILED DESCRIPTION

The present invention will now be described hereinafter in detail with reference to the accompanying drawings. The present invention is not, however, limited to the embodiments described herein; rather, these embodiments are intended to enable those skilled in this art to understand fully the invention.

As described above, the disclosure is directed to methods and associated apparatus for treating a subject in cardiac arrest. As used herein, the term "cardiac arrest" refers to all types of cardiac arrest, including ventricular fibrillation, asystole, and pulseless electrical activity. The subject of such cardiac arrest can be mammalian and more preferably human, but can be any animal that can be advantageously treated by oxygenating its brain and coronary vasculature during cardiac arrest.

Figure 1:
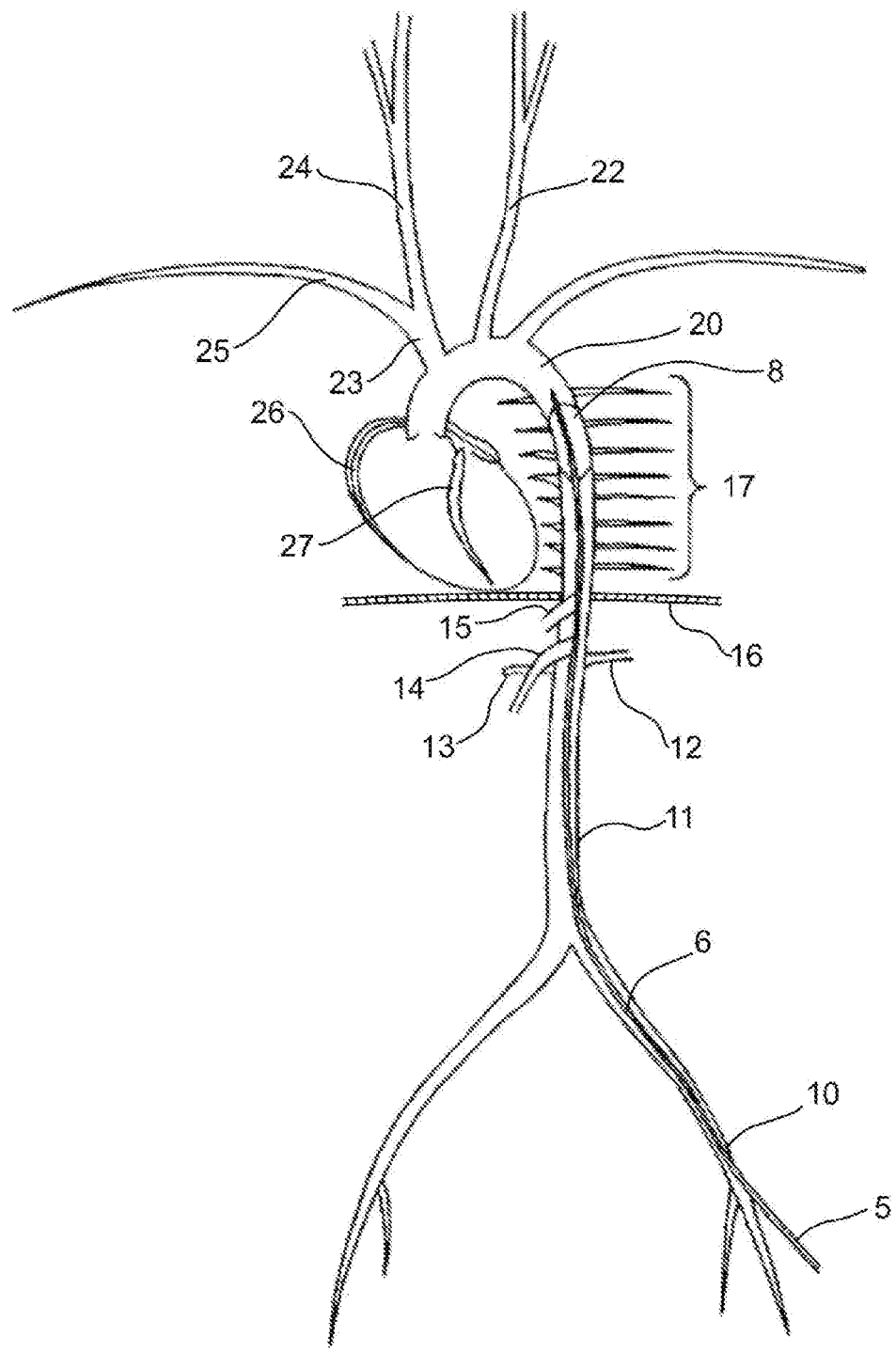
FIG. 1 is a schematic illustration of a balloon catheter inserted through the femoral artery into the aorta in a human subject proximal to the diaphragm but distal to the left subclavian artery, with the balloon inflated to block the descending aorta.

Blocking of the descending aorta, and infusion into the aortic arch, can be carried out with a balloon catheter unit such as that illustrated at 5 in FIG. 1. The balloon catheter unit 5 comprises an elongate catheter tube 6 having a primary lumen 7 through which protective solution may pass, and further comprises a balloon 8 at one end of the elongate tube 6 configured to be inflated to block the descending aorta of a human subject. A secondary tube 9 (or alternatively a secondary lumen formed in the wall of the tube 6 and extending longitudinally therewith) provides a mechanism for inflating the balloon 8 once the balloon 8 is positioned in the desired location within the descending aorta of the subject. A connector such as a Leur Lock™ fitting is provided at the end of the elongate tube 6 opposite the balloon 8 to connect the catheter tube 6 to a supply for the protective solution.

For a human adult, the size of the primary lumen 7 may be from 6 French to 14 French, the length of the catheter tube 6 may be from 50 to 150 centimeters, the inflated dimensions of the balloon 8 may be from 1.5 to 4 centimeters in diameter, the length of the balloon 8 may be from 2 to 10 centimeters, and the distance from the tip of the catheter tube 6 to the balloon 8 distance may be from 1 to 4 centimeters. For a human child, the lumen size may be from 5 French to 10 French, the catheter tube length may be from 20 to 80 cm, the balloon inflated dimensions may be from 0.75 to 2 cm in diameter, the balloon length may be 1.5 to 6 cm, and the catheter-tip to balloon distance may be from 0.5 to 2 cm. When inflated, the balloon 5 should be capable of withstanding a pressure of at least 300 to 500 mmHg to prevent leakage of protective solution down the descending aorta and rupture of the balloon during chest compression.

The catheter tube 6 may be made from a firm but somewhat flexible plastic material, and the balloon 8 from a latex or polyurethane material. The catheter tube 6 may be made from antithrombotic materials, such as having heparin bonding as a characteristic of construction, to inhibit formation of blood clots in the aorta. Reference may be made to U.S. Pat. Nos. 5,049,132; 5,049,131; 5,045,061; 5,042, 976; 5,041,125; and 5,216,032 for further guidance in the construction of the balloon catheter. It is specifically intended that the disclosures of all patent references cited herein be incorporated herein by reference.

Figure 2:
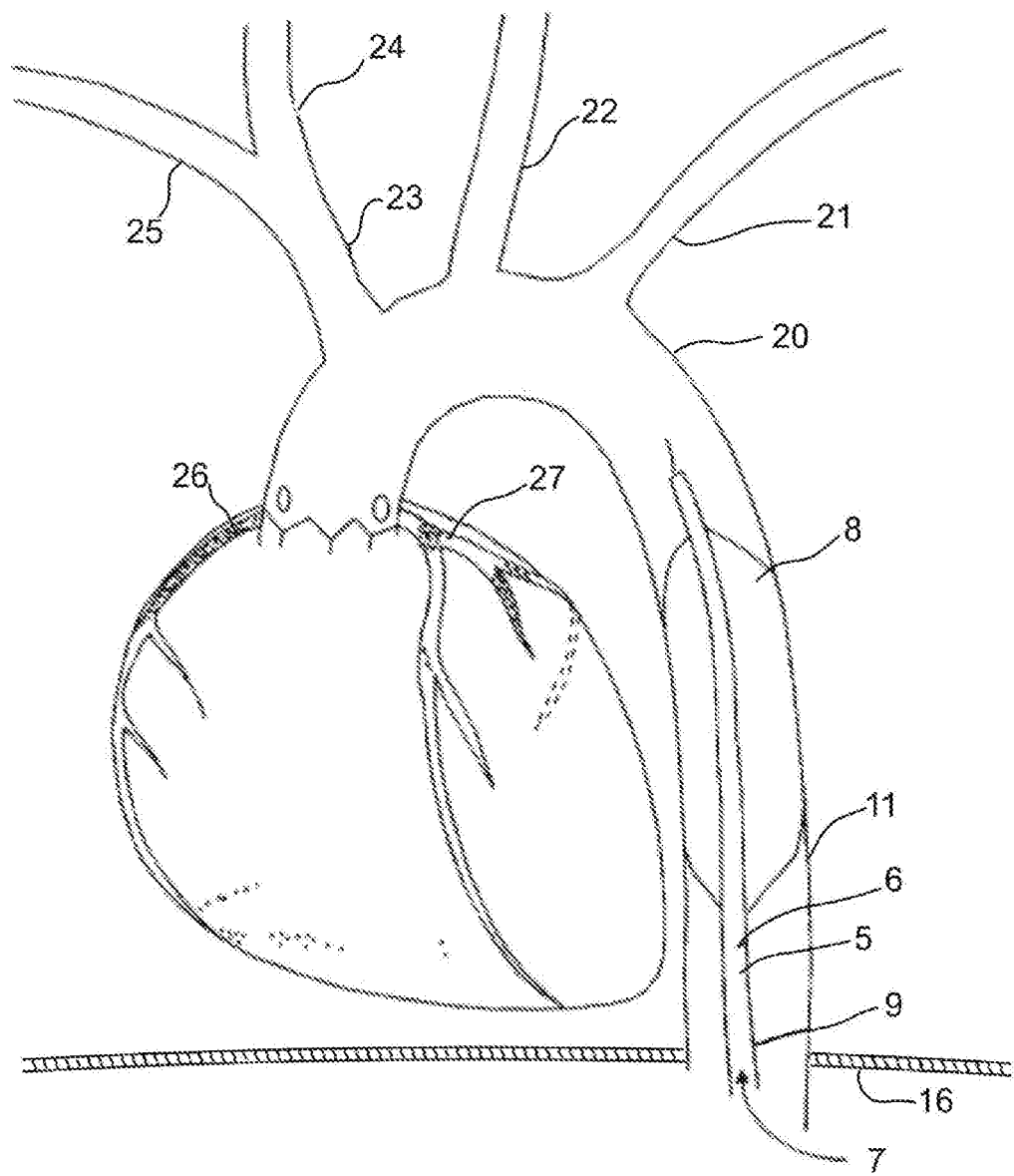
FIG. 2 is an enlarged partial view of the heart and balloon catheter of FIG. 1 showing the balloon catheter positioned to block the descending aorta and perfuse the aortic arch.

To block the descending aorta of the subject (FIGS. 1 and 2), the balloon catheter unit 5 is inserted into a femoral artery 10 of the subject and advanced within the descending aorta 11 past the renal arteries 12, 13, the superior mesenteric artery 14, the celiac trunk 15, the diaphragm 16, and past various ones of the intercostal arteries 17. The balloon 8 can be positioned distal to the carotid arteries 22, 24 and the left subclavian artery 21, but can be located at least proximal to the renal arteries 12, 13. The balloon 8 is inflated via the secondary tube 9 to block the descending aorta 11, with the leading end of the elongate tube 6 positioned to perfuse the aortic arch 20. In this position, protective solution pumped or forced through the balloon catheter unit 5 and exiting the balloon 8 will perfuse the left subclavian artery 21, the left common carotid artery 22, the brachiocephalic trunk 23 (and in turn the right carotid artery 24 and the right subclavian artery 25) and the coronary arteries 26, 27. Although some variations block the descending aorta with a balloon catheter as illustrated, those skilled in this art will appreciate that other means for blocking the descending aorta to prevent flow therein can also be used with the present invention.

Withdrawing the subjects blood can be carried out in any manner known to those skilled in this art to be suitable therefor. One technique of withdrawing autologous blood from the subject is to insert a catheter into the femoral vein (or some other large vein, such as the jugular vein or subclavian vein). This technique would allow blood to be continuously withdrawn and infused. Another technique would be to withdraw the blood from the proximal aorta with the balloon of the balloon catheter deflated. An alternative technique would involve withdrawing blood from the distal aorta with the balloon inflated, which is beneficial due to the capability of continuous infusion and withdrawal. A catheter embodiment for such withdrawal is illustrated schematically in FIG. 3. A balloon catheter unit 30 comprises two large lumens: an infusion lumen 31 that terminates beyond the balloon 32; and a blood withdrawal lumen 33 that terminates prior to the balloon 32. A balloon inflation line 34 terminates within the balloon 32. This embodiment enables blood to be withdrawn into the blood withdrawal lumen 33 either when the balloon 32 is deflated or inflated when the inlet 35 of the blood withdrawal lumen 33 is positioned in the distal aorta.

Once blood is withdrawn from the subject, it can be mixed with an anticoagulant to keep the blood from coagulating. Exemplary anticoagulants include heparin, acid citrate dextrose, or sodium citrate. Typically, the anticoagulant is simply added via a syringe to a conduit containing the withdrawn blood. Alternatively, anticoagulant can be added within a withdrawing catheter prior to the blood actually exiting the subject. A catheter configured for such use, designated at 36 is illustrated schematically in FIG. 4. An anticoagulant infusion line 37 terminates within and near the end of the blood withdrawal lumen 38. This catheter configuration enables anticoagulant to be introduced into the blood as the blood enters the catheter, and thus can reduce the degree of coagulation experienced by that blood. This catheter configuration can be combined with that described above in FIG. 3 to enable blood withdrawn from the distal aorta to receive anticoagulant just as it leaves the bloodstream.

After withdrawal, the blood is then oxygenated. Oxygenation can be performed in any manner known to those skilled in this art to oxygenate blood. For example, blood can be shunted into a tank or reservoir having an oxygen membrane and passed therethrough.

In a variation the withdrawn blood be passed through a filter or other device that removes any blood clots or other debris prior to reinfusion, as such debris can adversely affect perfusion.

Once the blood is oxygenated, it can be infused into the aorta of the subject. Typically between about 250 to 3000 milliliters of the blood are infused, with 750 to 2000 milliliters of the blood being a more preferred dosage. Perfusion should be carried out sufficiently rapidly to enhance cardiac electrical activity; in one variation, the perfusion duration is less than five minutes.

Perfusion of the newly-oxygenated blood can be carried out continuously, or preferably can be carried out in a pulsatile rhythm. Perfusion with a pulsatile rhythm can assist in removing sludged blood cells from the microvasculature of the subject and may have positive effects on resuscitation due to the rheology of blood. In particular, perfusion with a pulsatile rhythm in which the perfusion "pulses" are timed to coincide with the decompression or relaxation phases of CPR (diastolic pulsing) can be especially effective.

A vasoconstrictor may be employed in the methods described herein. Exemplary adrenergic vasoconstrictors include epinephrine, norepinephrine, methoxamine, phenylephrine, with epinephrine being preferred; nonadrenergic vasoconstrictors can also be used. Vasoconstrictors may be administered by any suitable means, such as by parenteral injection (e.g., intravenous injection, intraarterial injection, subcutaneous injection, intramuscular injection, intraperitoneal injection, tracheobronchial administration), or by including the vasoconstrictor in the protective solution used to perfuse the aortic arch. In a variation the administration of the vasoconstrictor be concurrent with (i.e., sufficiently close in time to) perfusion of the aortic arch so that the vasoconstrictor will affect coronary perfusion with the autologous blood. The dosage of the vasoconstrictor will vary depending on the subject and the particular vasoconstrictor chosen, but will generally be between 0.002 and 0.3 mg/kg.

Medicaments containing a vasoconstrictor for enhancing coronary perfusion with a protective solution during selective aortic arch perfusion may be prepared by contacting and mixing the vasoconstrictor with a pharmaceutically acceptable carrier, such as a sterile pyrogen-free saline solution, in accordance with techniques known in the pharmacy art. The pharmaceutical carrier may be the protective solution itself, such as a perfluorochemical blood-substitute solution as discussed above.

Restoring spontaneous circulation in the subject may be carried out by any suitable means, such as electric shock or precordial thump (i.e., application of an external force), or by enhancing electrical activity through perfusion and other resuscitation techniques so that normal electrical activity re-emerges without application of an external force. An electric shock to heart muscle tissue which will restore spontaneous circulation from a chaotic electrical signal (or "defibrillation") may be administered with any suitable defibrillator, such as the Responder™ 1500 (manufactured by Marquette Electronics, Milwaukee, Wis.).

Figure 3:
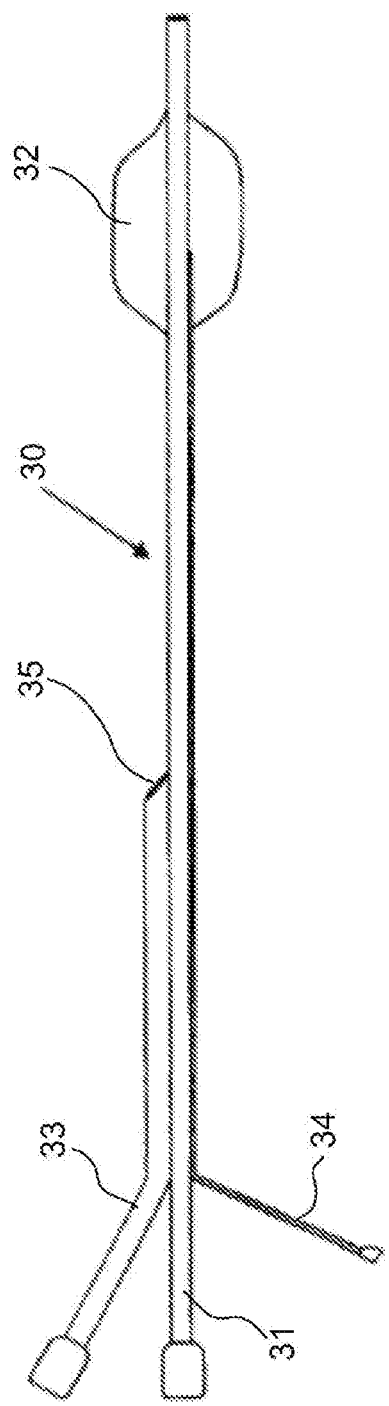
FIG. 3 is a schematic illustration of a triple lumen balloon catheter having a blood withdrawal line configured to withdraw blood from the distal aorta.
Figure 4:
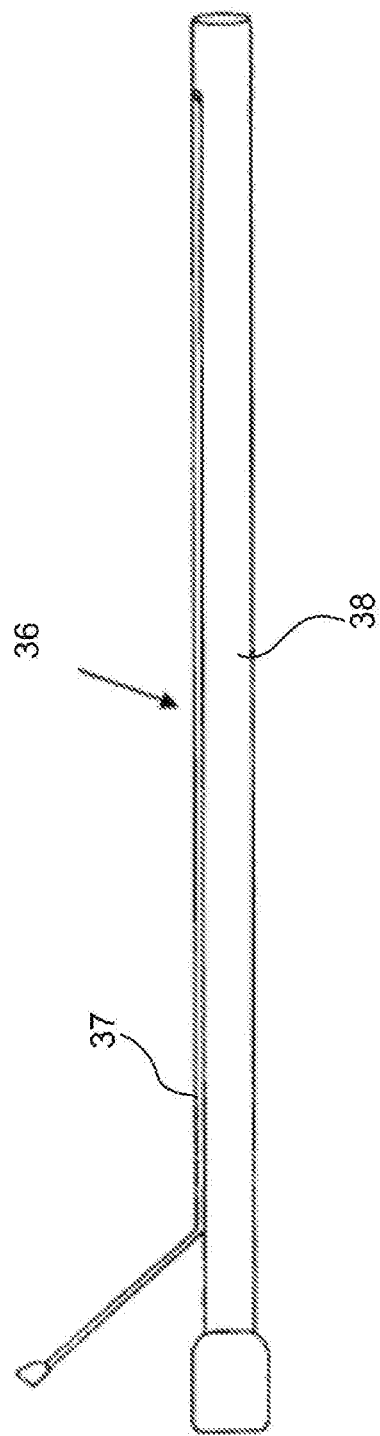
FIG. 4 is a schematic representation of a blood withdrawal catheter having an anticoagulant infusion port.
Figure 5:
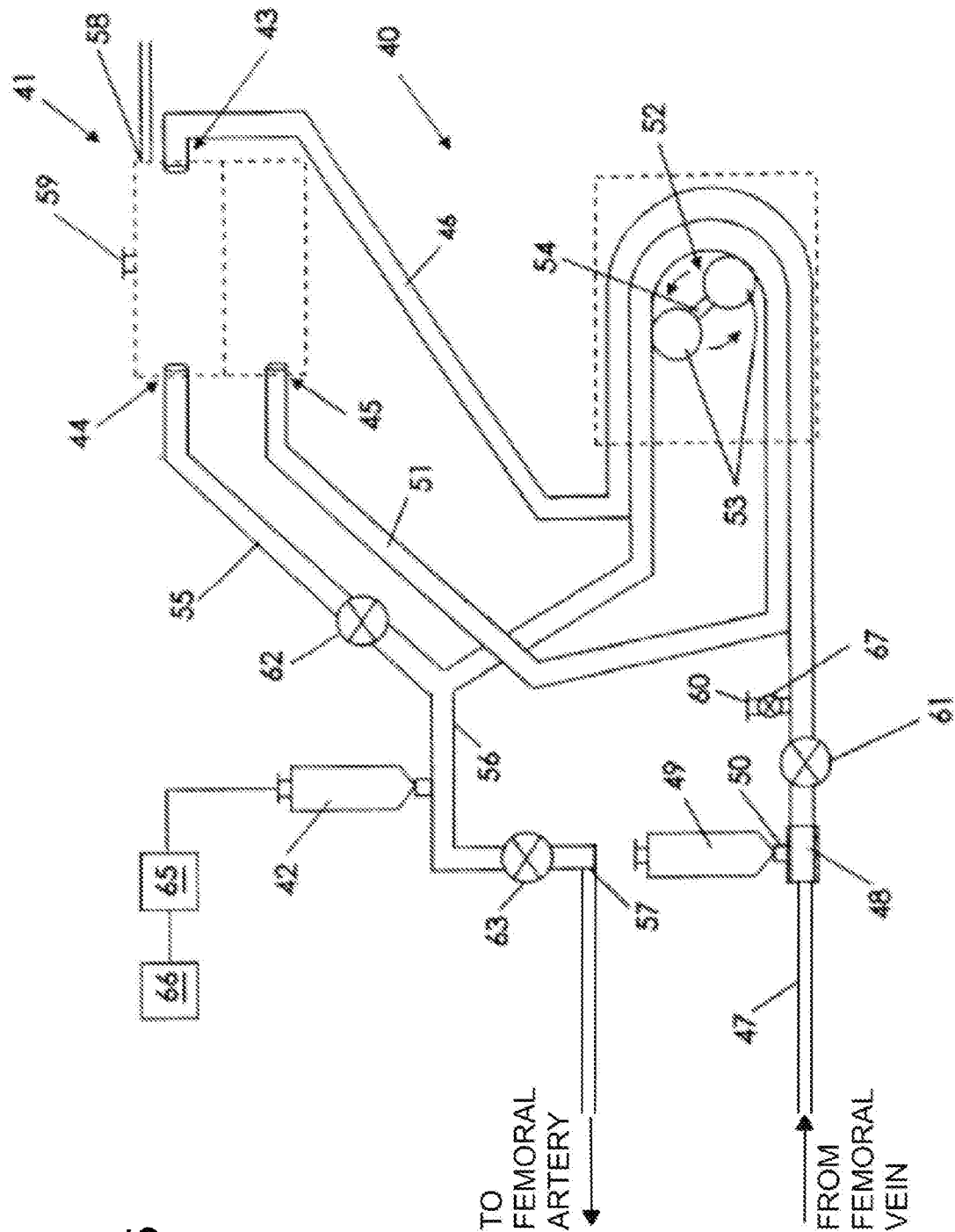
FIG. 5 is a schematic illustration of an exemplary SAAP system and its catheter extending into the femoral artery of a subject.

An exemplary SAAP apparatus 40 is schematically illustrated in FIG. 3. The apparatus 40 comprises a storage tank 41 having two upper ports 43, 44, and a lower port 45. A venous blood withdrawal line 46 is attached at one end to upper port 43 and at its other end to a venous blood withdrawal catheter 47 by a fitting 48. The venous blood withdrawal catheter 47 is to be inserted into the femoral vein of a subject. An anticoagulant syringe 49 is also fluidly connected to the fitting 48 via a catheter, connector, or connector tubing 50. An oxygenated blood infusion line 51 is attached at one end to the lower port 45. As the oxygenated blood infusion line 51 extends away from the lower port 45, it meets with and travels adjacent to the venous blood withdrawal line 46. The adjacent sections of the lines 46, 51 are enclosed within a roller pump apparatus 52, which comprises a pair of wheels 53 mounted on a rotary arm 54. Rotation of the arm 54 causes the wheels 53 to contact the lines 46, 51 and thereby deliver blood or a blood substitute to and from the SAAP apparatus 40. At its outlet end, the oxygenated blood infusion line 51 meets the outlet end of an oxygenated blood recirculation line 55 that extends thereto from the upper port 44. An infusion line 56 extends from the junction of the lines 51, 55 to an infusion port 57 that is connected to the inlet end of a balloon catheter (not shown) that is to be inserted in the femoral artery of a subject. A syringe 42 is fluidly interconnected with the infusion line 56. The storage tank 41 also includes an oxygen intake port 58 and an additional syringe port 59. The venous blood withdrawal line 46 also includes an oxygen intake port 60 between the fitting 48 and the roller pump apparatus 52. Three valves 61, 62, 63 are located, respectively, adjacent the fitting 48 on the venous blood withdrawal line 46, on the oxygenated blood recirculation line 55, and on the infusion line 56 between the syringe 42 and the infusion port 57. A fourth valve 67 is located on the oxygen intake port 60. A controller 65 is operably connected with the syringe 42 to control its operation and is also operably connected with a CPR device (indicated schematically at 66). The apparatus 40 may also include a valve (not shown) that can remove any air that enters the system prior to its being introduced into the subject's aorta.

In operation, autologous blood is drawn from the subject into the femoral venous blood withdrawal catheter 47. Anticoagulant, such as heparin, is added to the withdrawn blood through the anticoagulant syringe 49. The venous blood is pumped through the venous blood withdrawal line 46 by the roller pump apparatus 52; as the rotary arm 54 rotates, the wheels 53 provide a positive pressure of the blood that forces it through the line 46. The venous blood enters the storage tank 41 through upper port 43 and flows into the bottom portion of the storage tank 41. Oxygen is continuously introduced into the storage tank through the oxygen intake port 58. After the blood is oxygenated in the storage tank 41, it flows therefrom through the lower port 45 into the oxygenated blood infusion line 51. The blood is propelled by the action of the roller pump unit 52 to the infusion line 56. Flow into the oxygenated blood recirculation line 55 is prevented because the valve 62 is in a closed position Oxygenated blood can be furnished in a pulsatile rhythm by reciprocating action from the syringe 42. The oxygenated blood flows through the infusion line 56, through the infusion port 57, and into the SAAP catheter for delivery to the aorta.

Similarly, this apparatus 40 can also be used to deliver a blood substitute to the subject. See U.S. Pat. No. 5,216,032 to Manning for a discussion of blood substitutes. The blood substitute can be introduced into the storage tank 41 through the syringe port 59. The valves 61 and 62 are in their closed positions. The blood substitute follows the same path to the subject as that of oxygenated blood described above.

Further, the apparatus 40 can be used to recirculate, and thereby thermally and hemodynamically prepare a blood substitute for perfusion. For recirculation of blood substitute, valve 63 is in its closed position, and valve 62 is in its open position. This creates a closed loop system that proceeds from the storage tank 41 to the oxygenated blood infusion line 51, the recirculation line 55, and the upper port 44 before returning to the storage tank 41.

Use of the apparatus 40 is exemplified by the following scenario. A physician arrives at the scene of a cardiac arrest patient and secures access to the femoral artery by either percutaneous or surgical means. The blood substitute is oxygenated during the vascular access procedure. The catheter is advanced to the thoracic aorta and epinephrine is administered into the aortic arch. The catheter balloon is inflated and an initial SAAP infusion of the blood substitute (which can contain reperfusion-injury combating agents) is performed. An initial bolus of blood substitute is rapidly infused to close the aortic valve and CPR is halted for the initial infusion lasting 30 to 60 seconds. This would assure that the myocardium was effectively perfused with the blood substitute. During this initial infusion, access to a femoral vein is secured. Aortic arch epinephrine administration can be titrated to maximize CPR-diastolic coronary perfusion pressure (CPP). Two to three minutes after the initiation of the first blood substitute infusion, a second blood substitute infusion is initiated. Pulsed diastolic infusion induced by the syringe 42 using half of the volume initially infused would be used to elevate CPP and diminish the volume effects of a second infusion. The infusion pulses are administered during the decompression and relaxation phases of CPR. During the second blood substitute infusion, femoral blood is withdrawn, anticoagulated via the anticoagulant syringe, oxygenated in the storage tank 41, thermally treated (if necessary), and filtered in preparation for reinfusion. Depending upon the rapidity of femoral venous access and blood withdrawal, either a third blood substitute infusion similar to the second or an autologous blood infusion is initiated. Aortic arch epinephrine titration, other pharmacologic therapies, and repetitive or continuous autologous blood SAAP can be performed until return of spontaneous circulation (ROSC) is attained or the resuscitative efforts are halted. If ROSC is attained, autologous blood withdrawal and reinfusion could be continued (with or without the catheter balloon inflated depending, on the clinical situation) serving as partial cardiopulmonary bypass support for the still unstable cardiovascular system in the early post-resuscitation phase. Graded balloon inflation could be used to provide peripheral resistance as needed in the immediate and early post-resuscitation phase.

In view of the considerable out-of-hospital use anticipated with the present invention, in a variation the SAAP apparatus be packaged to be easily portable. The apparatus can be packaged in a suitcase, attache case, backpack, or the like, and be easily carried to the patient for use by a physician or paramedic.

The present invention may be beneficial in the management of traumatic and other nontraumatic/surgical causes of cardiac arrest or profound hypovolemia with impending cardiac arrest. In addition to rapid volume replacement, the catheter balloon could serve much like an aortic cross-clamp to significantly reduce or stop exsanguinating hemorrhage from the abdomen, pelvis, or lower extremities until the patient could be transferred to the operating room. Clinical situations where the present invention can be used include: blunt abdominal or multi-system trauma with profound hemorrhage/hypovolemia; penetrating abdominal trauma with profound hemorrhage/hypovolemia; ruptured abdominal aortic aneurysm with profound hypotension or impending arrest; and major pelvis fractures or disruption. In hemorrhagic/hypovolemic conditions, heterologous human blood, such as from a blood bank, may also be employed.

Turning now to improved variations, the following devices and/or methods further assist in techniques for resuscitating a patient. The devices, methods, systems and other disclosure contained in U.S. Provisional No. 61/727,302 filed on Nov. 16, 2012 are incorporated by reference in its entirety.

Figure 6A:
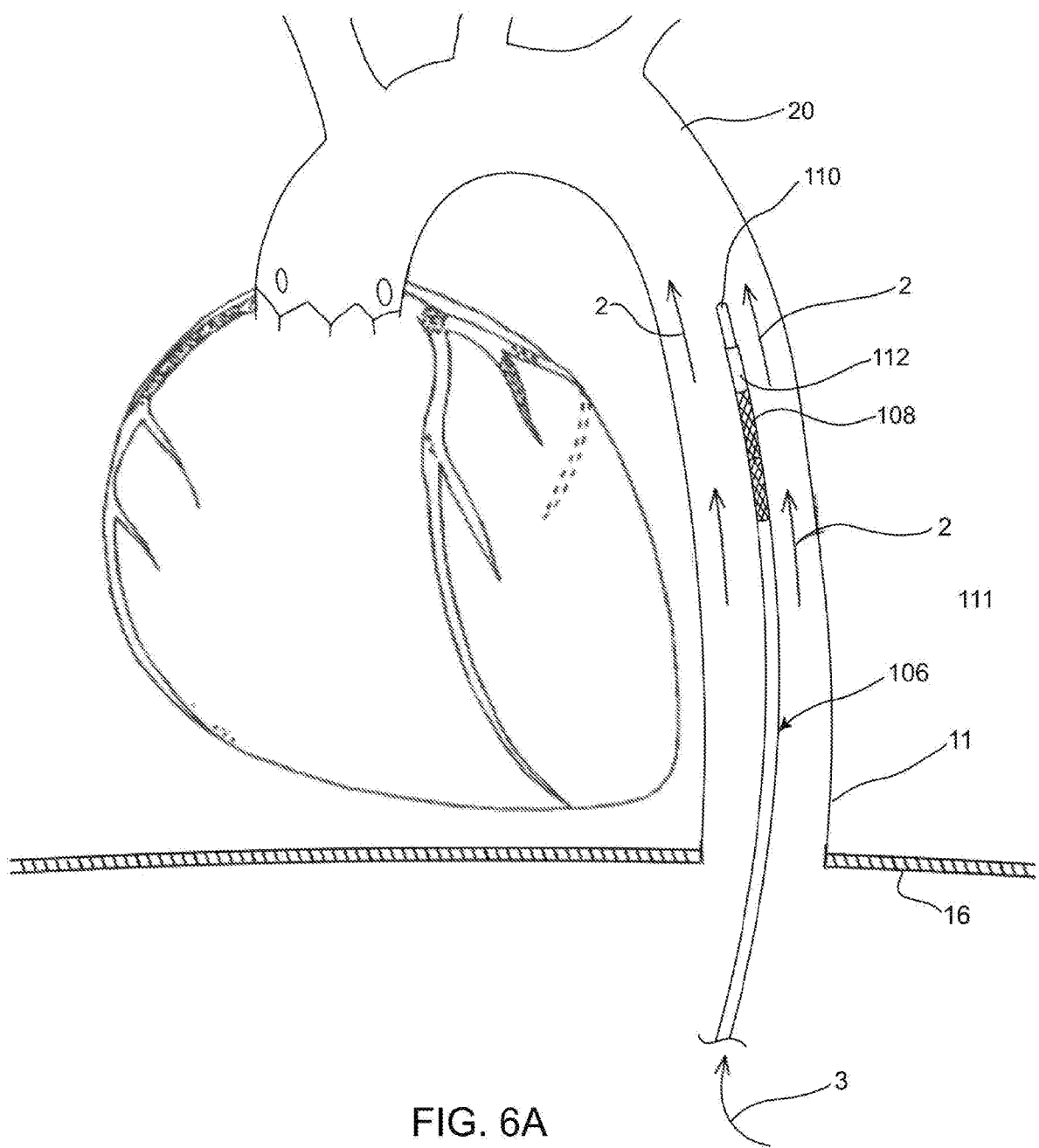
FIGS. 6A and 6B illustrate variations of devices that rely on a perfusion substance to inflate an occlusive expandable member.
Figure 6B:
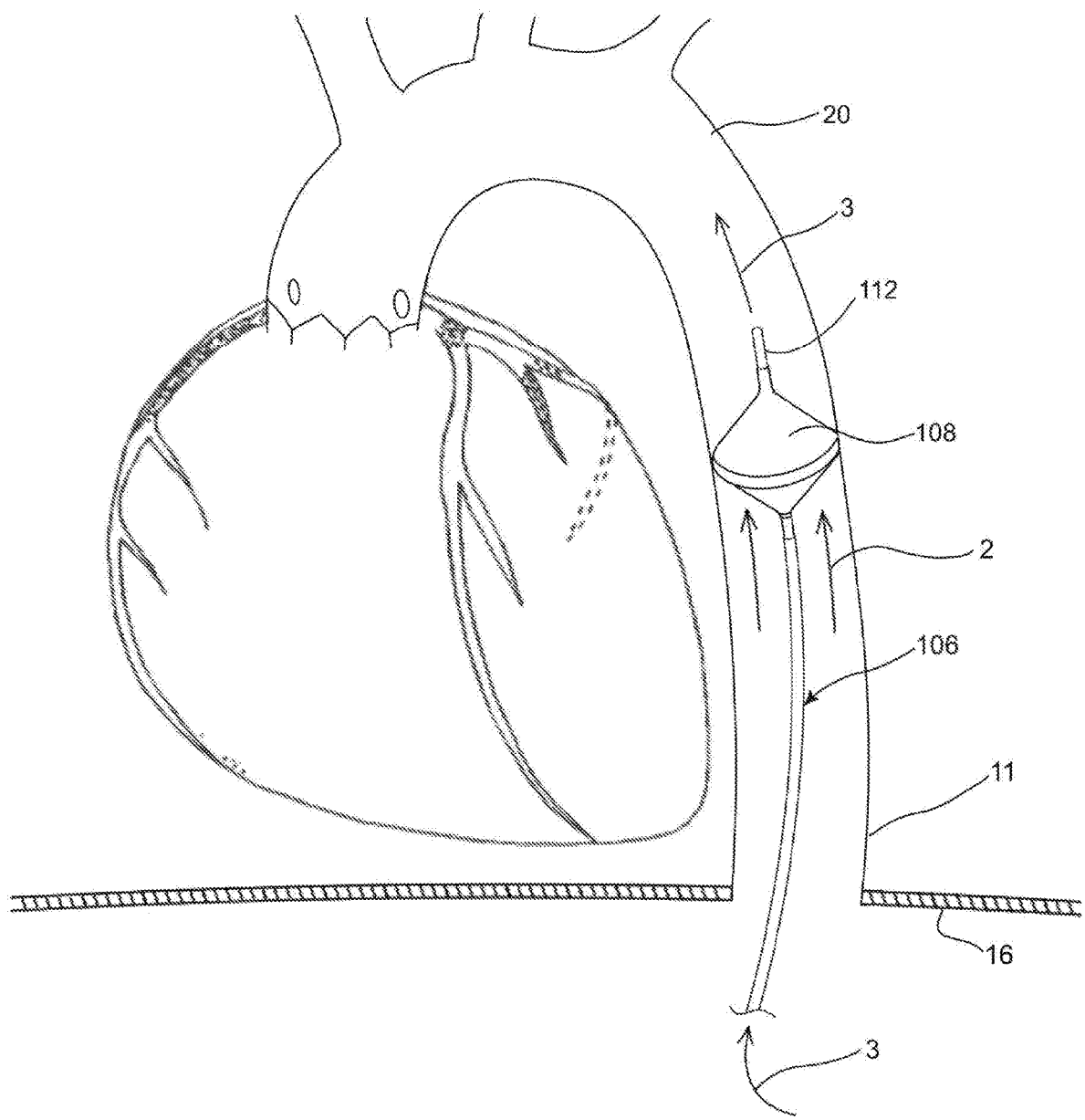

FIG. 6A illustrates another variation of a device 106 having an expandable member 108, where the device is positioned within the aorta 11 such that the distal end 112 is positioned within arterial flow of blood 2 within the aorta 11. As illustrated in FIG. 6A, an infused substance 3 is infused within a lumen of the device 106. Typically, the infused substance comprises infused blood. However, other substances are within the scope of this disclosure. Regardless, flow of the infused substance within the catheter 106 is diverted within the expandable member 108. The diversion can be accomplished in any number of ways, for example, an obturator 110 can be positioned within the device 106 to increase a fluid flow resistance at the distal end 112 of the device 106. The obturator 110 can include an expandable member, a taper or other structure to prevent or resist the flow of the infused substance from the distal end 112 of the device 106. The increased resistance to flow causes the infused substance to flow into an expandable member 108, as shown in FIG. 6B. Expansion of the expandable member 108 causing interruption of arterial flow 2. Flow of the infused substance can occur in a space between the device 106 and the obturator 110. Alternatively, the obturator 110 can include one or more lumens to provide flow of blood into the expandable member. In additional variations, the obturator can include one or more lumens for a guidewire or other such device. In an additional variation, the expandable member 108 can be located on a recess on the device 106 such that a diameter of the expandable member in a reduced profile is no greater than a diameter of the catheter body of the device.

Figure 7A:
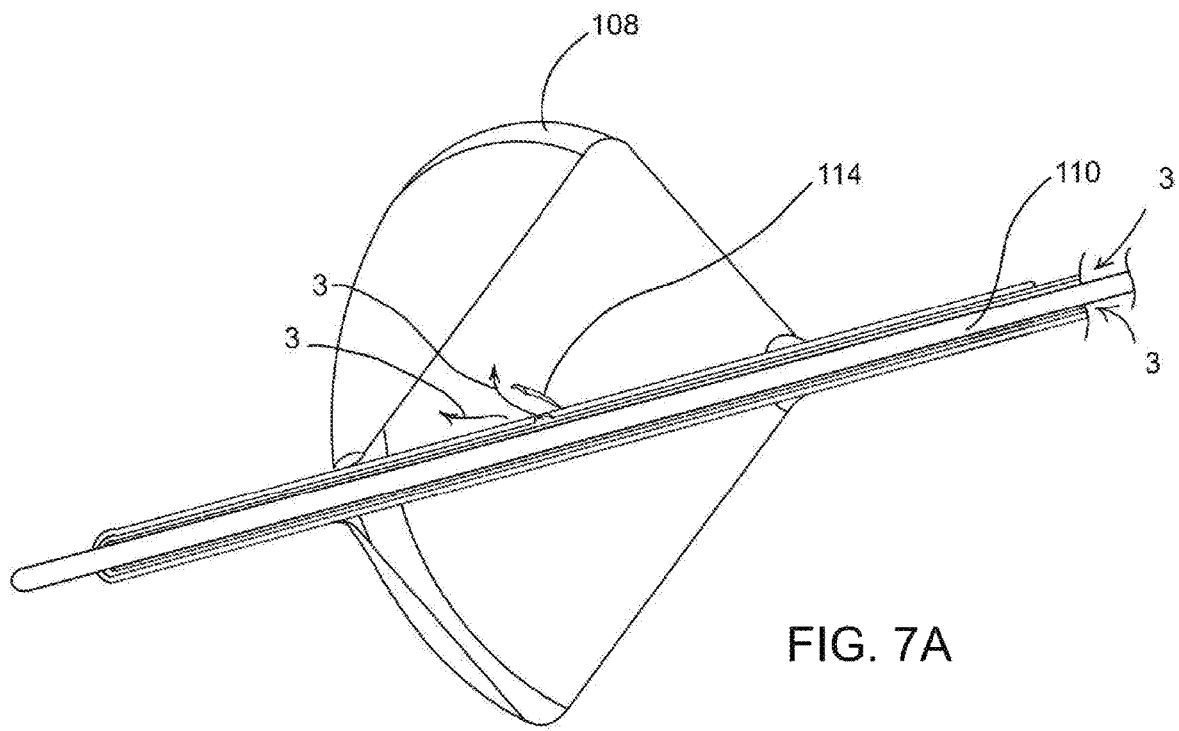
FIGS. 7A and 7B illustrate a partial cross sectional view of the expandable member showing a valve located within the expandable member.

FIG. 7A illustrates a partial cross sectional view of the device 105 with an obturator 110 extended therethrough when a flow of an infusion substance 3 is diverted into the expandable member 108. As illustrated, the device 106 can include one or more valves 114. The valves can be any structure that permits flow of the infusion substance 3 into the expandable member 108 and prevents the infusion substance from leaving the expandable member until desired. In one example, the valve can comprises a reed valve.

Figure 7B:
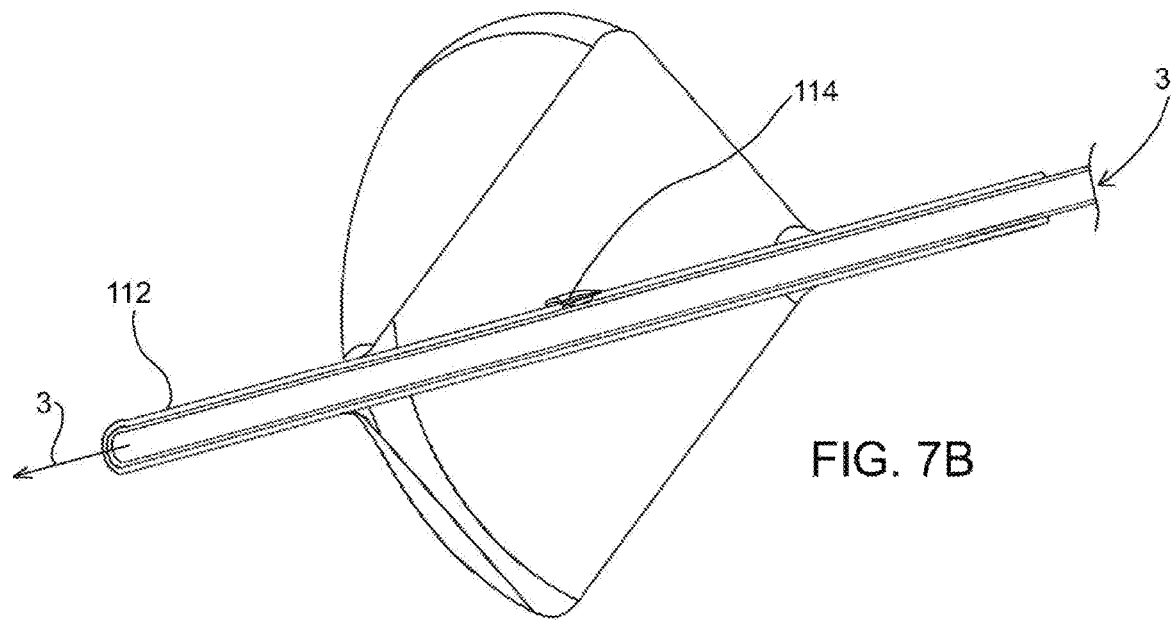

Once the expandable member 108 is sufficiently expanded, either by forming a seal against the walls of the vessel to stop arterial blood flow, reaching a desired pressure, delivery of a volume of the infusion substance, etc. the flow resistance at the distal end 112 of the device 106 can be reduced (e.g., by removing the dilator as shown in FIG. 7B) such that the flow of the infusion substance 3 extends through the device 106 and out of the distal end 112. In alternate variations, the dilator 110 can remain within the occlusion device 106 such that when pressure in the expandable member 108 reaches a threshold value, flow of the infusion substance is automatically directed through the distal end 112.

Figure 8A:
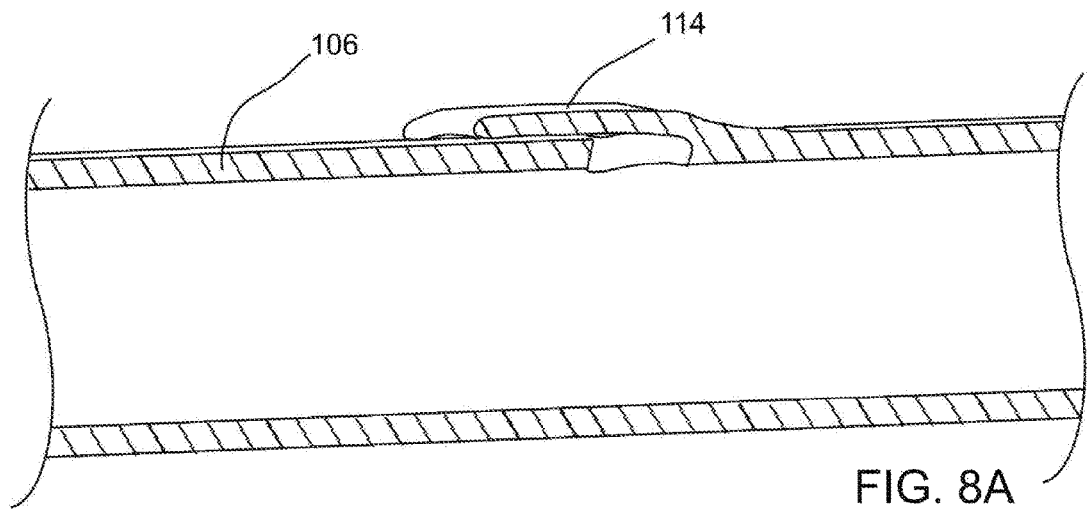
FIGS. 8A and 8B illustrate the valve in a closed position and in a released position using a release mechanism.

FIG. 8A illustrates a portion of the device 106 without the expandable member. As shown, the valve 114 is in a closed position and allows flow of the infusion material from within the lumen of the device 105 into the expandable member. The valve 114 remains closed in the absence of pressure or flow from the device 106 lumen such that fluid within the expandable member cannot exit through the valve.

Figure 8B:
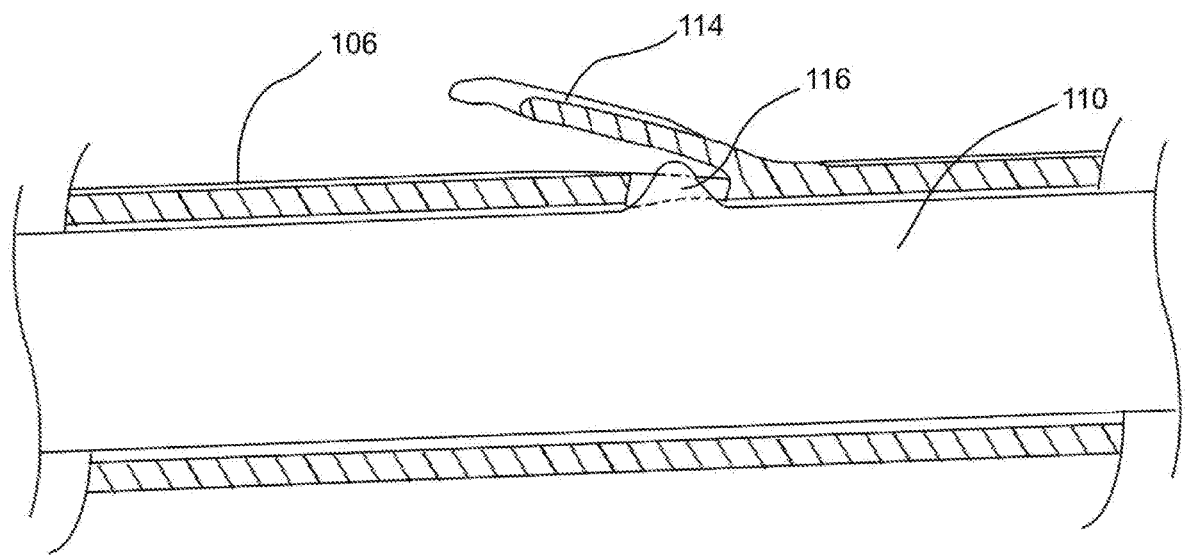

FIG. 8B illustrates a variation of the device 106 using a valve release mechanism 115 to open the valve and reduce the expandable member. The release mechanism can comprise any spring loaded structure that opens the valve 116 (or a separate valve). In one variation, the release mechanism 116 can be located on a portion of the dilator 110, such that a physician can position the release mechanism 116 adjacent to the valve 114 when desired. Clearly, alternate variations of the device include a separate release mechanism.

The device described above provides an improvement over conventional devices by maximizing the internal size of the infusion lumen while minimizing the external size of the catheter by eliminating the need for a separate inflation lumen. In additional variations, the obturator or device used to expand the expandable member can be a color that is different than a color of the device used to drain the expandable member. For example, the obturator can be green while the draining obturator can be red.

Any of the variations described above can include an indicator that the expandable member is in the expanded state. Such an indicator could prevent attempted removal of the device from the vessel when expanded. The indicator can be a radiopaque marking, or other conventional tag to provide the status of the expandable member to the user.

Naturally, the system may include a variation of the above configurations. Variations of the device may include systems that have various decorations on the outer surface to make the system more child-friendly and alleviate apprehension of getting an injection. In these devices and methods, the conditions may be those as described above, or other conditions as required by the specific treatment sought.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A method of resuscitating a patient consisting:
   accessing an arterial vessel;
   positioning a catheter into the arterial vessel;
   advancing the catheter through the arterial vessel to position it below a vessel supplying blood to a heart and a brain;
   providing a flow of infused blood through the catheter;
   increasing a resistance of fluid flow at a distal end of the catheter such that the flow of infused blood expands an expandable portion of the catheter to prevent arterial blood from flowing past the expanded portion in the arterial vessel; and
   reducing the resistance of fluid flow at the distal end of the catheter such that the infused blood exits the distal end of the catheter and the arterial vessel between the heart and the expandable portion of the catheter.

2. The method of claim 1 where the accessing the arterial vessel involves identifying the location of the arterial vessel by a technique selected from the group consisting of: a) feeling for a pulse and inserting the access device at the pulse; b) using ultrasound; c) using an electric field; d) using a magnetic field disturbance; and e) using tissue density differences.

3. The method of claim 1 where positioning the catheter further comprises:
   placing a needle through the skin and overlying tissue into the arterial vessel;
   placing a wire through the needle; and
   placing the catheter over the needle or over the wire after removing the needle.

4. The method of claim 1 further comprising determining the position below the vessel supplying blood to the heart and the brain by a technique selected from the group consisting of: a) determining the distance from the access site to a desired position external to the patient and advancing the catheter to said predetermined distance; b) using xray to place the catheter into appropriate position and to verify that the catheter is in appropriate position; c) detecting a signal from the catheter using a modality selected from the group consisting of light, sound, ultrasonic, heat, cold, and electromagnetic energy to determine placement position.

5. The method of claim 1 where the expandable portion of the catheter comprises a device selected from the group consisting of a) a balloon catheter; b) a catheter with an umbrella structure; c) a catheter having a mechanically expanding spheroid.

6. The method of claim 1 where providing the flow of infused blood through the catheter comprises additionally infusing a substance selected from the group comprising an oxygen carrier such as a perflourocarbon, calcium substance, EDTA, a saline fluid, a cooling fluid and a warming fluid.

7. The method of claim 1 where the flow is continuous.

8. The method of claim 1 where the flow is pulsatile.

9. The method of claim 1 where the flow is at a rate and or pressure sufficient to close the aortic valve.

\* \* \* \* \*